United States Patent
Vishnu Newadkar et al.

(10) Patent No.: US 8,927,743 B2
(45) Date of Patent: Jan. 6, 2015

(54) PROCESS FOR OBTAINING DRONEDARONE

(75) Inventors: Ravindranath Vishnu Newadkar, Thane Maharashtra (IN); Avinash Changdeo Gaikwad, Majiwade Thane Maharashtra (IN); Ajay Madhukar Harad, Kalyan (IN)

(73) Assignee: Laboratorios Lesvi, S.L., Barcelona (ES)

(*) Notice: Subject to any disclaimer, the term of this patent is extended or adjusted under 35 U.S.C. 154(b) by 0 days.

(21) Appl. No.: 13/880,162

(22) PCT Filed: Oct. 18, 2011

(86) PCT No.: PCT/EP2011/068202
§ 371 (c)(1),
(2), (4) Date: Jun. 11, 2013

(87) PCT Pub. No.: WO2012/052448
PCT Pub. Date: Apr. 26, 2012

(65) Prior Publication Data
US 2013/0289287 A1     Oct. 31, 2013

Related U.S. Application Data

(60) Provisional application No. 61/406,206, filed on Oct. 25, 2010.

(30) Foreign Application Priority Data

Oct. 21, 2010   (EP) .................................... 10188336

(51) Int. Cl.
*C07D 307/80*   (2006.01)
*C07D 307/81*   (2006.01)

(52) U.S. Cl.
CPC ............ *C07D 307/81* (2013.01); *C07D 307/80* (2013.01); *C07D 55/07* (2013.01)

USPC .......................................................... 549/468

(58) Field of Classification Search
CPC .................................................... C07D 307/80
USPC .......................................................... 549/468
See application file for complete search history.

(56) References Cited

U.S. PATENT DOCUMENTS

| 5,223,510 A | 6/1993 | Gubin et al. |
| 2005/0245524 A1 | 11/2005 | Noronha et al. |
| 2006/0115516 A1 | 6/2006 | Pearson et al. |
| 2010/0204470 A1 | 8/2010 | Wieser et al. |

FOREIGN PATENT DOCUMENTS

WO    WO-0248078 A1    6/2002

OTHER PUBLICATIONS

Disclosed Anonymously, "Solid state forms of (N-(2-butyl-3-(4-(3-(dibutylamino)proxy)benzoyl)benzofuran-5-yl)methanesulfonamide hydrochloride", ip.com PriorArtDatabase (http://priorartdatabase.com/IPCOM/000193200), Feb. 14, 2010, 7 pages.

Marzi, Elena, "International Search Report", for PCT/EP2011/068202 as mailed Dec. 22, 2011, 5 pages.

Baxter, N.J., et al "Reactivity and Mechanism in the Hydrolysis of β-Sultams" Journal of the American Chemical Society, vol. 122, No. 14, Apr. 12, 2000, pp. 3375-3385.

*Primary Examiner* — Taofiq A Solola
(74) *Attorney, Agent, or Firm* — Winstead PC

(57) ABSTRACT

The present invention provides a process for obtaining dronedarone or salts thereof characterized in that in an organic phase comprising one or more non-polar solvents, 5-amino-3-[4-(3-di-n-butylaminopropoxy)benzoyl]-2-n-butyl-benzofuran is reacted with methane sulfonyl chloride without the addition of a base. The invention also provides a process for obtaining intermediates of dronedarone environmentally friendly and industrially viable.

10 Claims, No Drawings

PROCESS FOR OBTAINING DRONEDARONE

FIELD OF THE INVENTION

The present invention is directed to an improved process for obtaining dronedarone.

BACKGROUND OF THE INVENTION

Dronedarone or N-[2-Butyl-3-[4-[3-(dibutylamino)propoxy]benzoyl]-5-benzofuranyl]-methanesulfonamide is a class III antiarrhythmic, chemically related to amiodarone developed by Sanofi-Aventis. It prolongs the duration of action potentials and has antiadrenergic and coronary vasodilatory effects. It is launched in the US as dronedarone hydrochloride under the tradename MULTAQ. This drug is indicated in adult stable patients with history of, or current non-permanent atrial fibrillation (AF) to prevent recurrence of AF or to lower ventricular rate.

Its chemical structure is as follows:

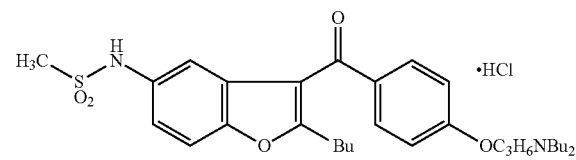

Dronedarone Hydrochloride

Dronedarone was first described in U.S. Pat. No. 5,223,510 as well as its therapeutic applications. U.S. Pat. No. 5,223,510 describes methods for preparing 3-[4-(aminoalkoxy)benzoyl]benzofuran or benzo[b]thiophene derivatives. In this patent, dronedarone hydrochloride is prepared from 2-n-butyl-3-(4-hydroxybenzoyl)-5-nitrobenzofuran as depicted in Scheme 1 below:

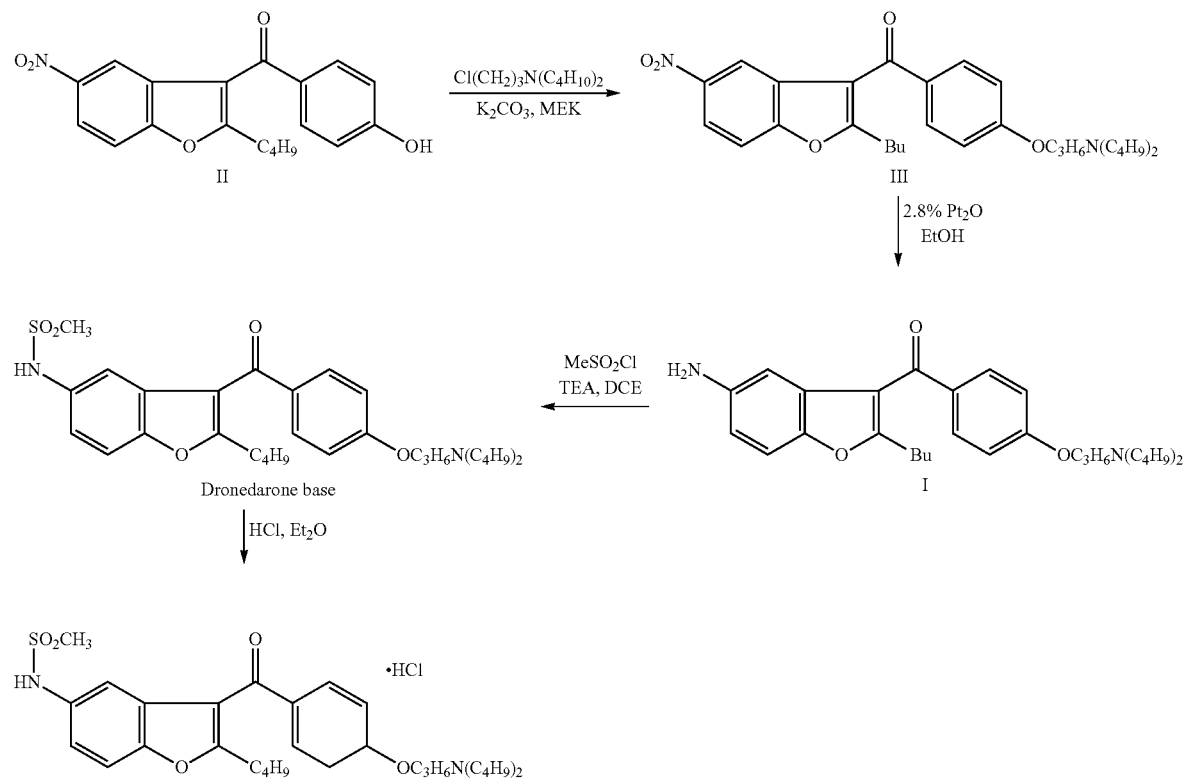

This method presents some disadvantages, in particular, long reaction times, the use of halogenated solvents which are toxic and environmentally harmful, and tedious purification methods such as column chromatography.

Therefore, there is not still an industrial method for obtaining dronedarone or its pharmaceutically acceptable salts, using safe, easily accessible and inexpensive reactants and solvents.

BRIEF DESCRIPTION OF THE INVENTION

The present inventors have surprisingly found a process for obtaining dronedarone or its pharmaceutically acceptable salts which is industrially viable, environmentally friendly and efficient.

Thus, the present invention relies on a process for obtaining dronedarone or pharmaceutically acceptable salts thereof

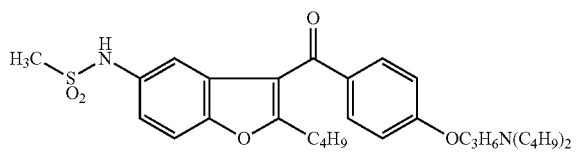

Dronedarone

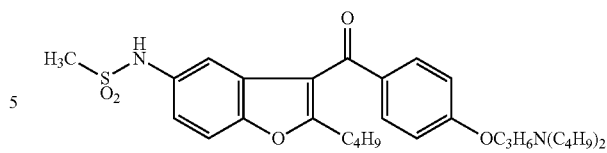

Dronedarone characterized in that, in an organic phase comprising one or more non-polar solvents, 5-amino-3-[4-(3-di-n-butylamino-propoxy)benzoyl]-2-n-butylbenzofuran (I) is reacted with methane sulfonyl chloride without the addition of a base, to give dronedarone, which, if desired, can be reacted with an organic or inorganic acid to form a pharmaceutically acceptable salt of dronedarone.

characterized in that, in an organic phase comprising one or more non-polar solvents, 5-amino-3-[4-(3-di-n-butylamino-propoxy)benzoyl]-2-n-butylbenzofuran (I) is reacted with methane sulfonyl chloride without the addition of a base to give dronedarone, which, if desired, can be reacted with an organic or inorganic acid to form a pharmaceutically acceptable salt of dronedarone.

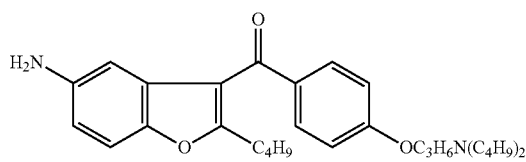

I

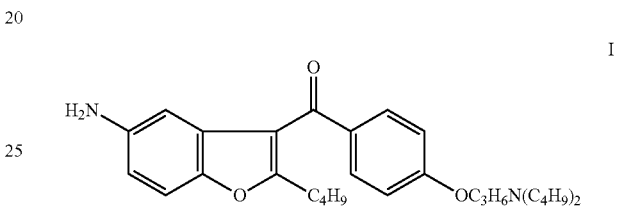

I

DESCRIPTION OF THE INVENTION

Definitions

In the context of the present invention, the following terms have the meaning detailed below:

The term "non-polar solvents" include, but are not limited to, toluene, xylene, n-heptane, octane, isooctane, cyclohexane, pentane and 1,4-dioxane. In one preferred embodiment, the non-polar solvent is toluene.

The term "strong base" refers to a basic chemical compound that is able to deprotonate weak acids in an acid-base reaction. Common examples of strong bases are the hydroxides of alkali metals and alkaline earth metals. Strong bases are even able to deprotonate weakly acidic C—H groups in the absence of water. As examples of strong bases may be mentioned potassium hydroxide, barium hydroxide, cesium hydroxide, sodium hydroxide, strontium hydroxide, calcium hydroxide and lithium hydroxide.

The term "base" used in the expression "without the addition of a base" refers to any organic base. As examples of organic bases there may be mentioned tertiary amines (trimethylamine, triethylamine, diisopropylethylamine, tributylamine, N-methylmorpholine and 1,4-diazabicyclo[2.2.2]octane), aromatic amines (pyridine, 2-methyl-5-ethylpyridine, 2,6-di-tert-butylpyridine, 4-dimethyl aminopyridine, imidazole and 1-methylimidazole), cyclic amidines (1,8-diazabicyclo[5.4.0]-7-undecene, 1,5-diazabicyclo[4.3.0]-5-nonene), alkali metal alkoxides (lithium methoxide, sodium methoxide, potassium methoxide, lithium ethoxide, sodium ethoxide, potassium ethoxide and lithium tert-butoxide) and alkali metal amides (lithium diisopropylamide, lithium hexamethyldisilazide, potassium hexamethyldisilazide).

DESCRIPTION

The present invention deals with a process for obtaining dronedarone or pharmaceutically acceptable salts thereof According to the prior art, the preparation of dronedarone crude from 5-amino-3-[4-(3-di-n-butylamino-propoxy)benzoyl]-2-n-butylbenzofuran (I) lasts 20 hours and after that time, the resulting crude is purified by column chromatography (61.6% yield). Example 3 of U.S. Pat. No. 5,223,510 describes the preparation of dronedarone from 5-amino-3-[4-(3-di-n-butylamino-propoxy)benzoyl]-2-n-butylbenzofuran (I). Step a) of US'510 describes the formation of the sulfonamido moiety by adding a solution of methane sulfonyl chloride in dichloroethane to a solution of 5-amino-3-[4-(3-di-n-butylamino-propoxy)benzoyl]-2-n-butylbenzofuran (I) and triethylamine in dichloroethane. However, the present inventors have reproduced this example, in particular step a), but the reaction did not go to completion, even after using excess of triethylamine or after changing the solvent (dichloromethane or acetonitrile).

According to that example 3, the product thus obtained is treated with hexane to give a crystalline fraction with an HPLC purity of 96.1%. Step b) of US'510 prepares the hydrochloride salt of dronedarone by treating a solution of dronedarone in ethyl acetate with hydrogen hydrochloride in ether.

Surprisingly, the present inventors have found that when the reaction is performed using non-polar solvents and without the addition of any base, dronedarone is obtained in good yields and purity with no need of column chromatography purification. In addition, the yield and purity obtained are reproducible when increasing the amount of starting material. Therefore, the process of the invention is appropriate for obtaining dronedarone or its salts in an industrial scale. In comparison to the method of the prior art, the reaction is complete in less than 10 hours, preferably in less than 5 hours, most preferably in 3 hours or less.

The process of the invention is carried out in the presence of a non-polar solvent or mixtures thereof. The non-polar solvent may be selected from toluene, xylene, n-heptane, octane, isooctane, cyclohexane, pentane, benzene and 1,4-dioxane. Preferably, the solvent is toluene.

The reaction temperature is the reflux temperature of the solvent or mixtures of solvents used in the process. For example, if the process uses toluene, the reflux temperature is 110° C.

The mixture obtained upon completion of the reaction contains dronedarone. This mixture may be subjected to a post-treatment such as washing and extraction. Dronedarone may be isolated by ordinary isolating processes like concentration or crystallization.

Optionally, dronedarone may be converted into an acid addition salt. The acid used to obtain an acid addition salt of dronedarone may be, for example, formic acid, oxalic acid, fumaric acid, maleic acid, succinic acid, malic acid, citric acid, acetic acid, lactic acid, tartaric acid, etc.; or an inorganic acid such as hydrochloric acid, hydrobromic acid, sulphuric acid, phosphoric acid or nitric acid. Most preferred acid is hydrochloric acid. The desired salt may be isolated by filtration if it precipitates from the solution or by evaporation to recover the salt.

When hydrochloric acid is used, it may be added in the form of a gas or in an aqueous or ethereal solution. Alternatively, hydrogen chloride may be generated in situ by the addition of trimethylsilyl chloride to a solution of dronedarone base in the presence of alcohols or water. When using the trimethylsilyl alternative, dronedarone base is first solved in ethyl acetate, preferably it is solved in 20-40 volumes (g dronedarone per L of solvent) of ethyl acetate. Preparation of crystalline dronedarone hydrochloride may be afforded as taught in IPCOM000193200D published anonymously in 14 Feb. 2010. For example, dronedarone hydrochloride is solved in acetone while heating at reflux. The resulting solution is allowed to cool at room temperature (25-30° C.) to crystallize. Crystals may be filtered off and dried. Other suitable solvents for obtaining crystalline dronedarone hydrochloride are acetonitrile and isopropyl alcohol.

In an embodiment of the present invention it is provided a process for obtaining dronedarone or its salts from 2-n-butyl-3-(4-hydroxybenzoyl)-5-nitrobenzofuran (II) by the following steps:

a) condensation of 2-n-butyl-3-(4-hydroxybenzoyl)-5-nitrobenzofuran (II)

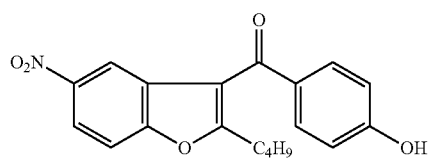

II with N,N-butyl-3-chloro-1-propanamine in water in the presence of a strong base to form 2-n-butyl-3-[4-(3-di-n-butylaminopropoxy)benzoyl]-5-nitrobenzofuran (III),

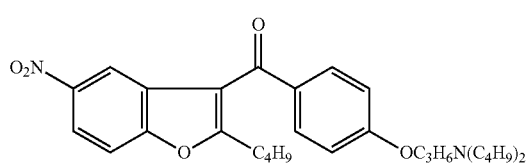

III and, b) catalytic reduction of compound III to obtain compound 5-amino-3-[4-(3-di-n-butylamino-propoxy)benzoyl]-2-n-butylbenzofuran (I)

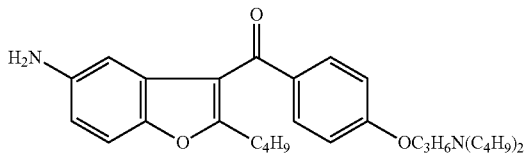

I

The condensation step a) is carried out in the presence of water and a strong base. The strong base is selected from potassium hydroxide, barium hydroxide, cesium hydroxide, sodium hydroxide, strontium hydroxide, calcium hydroxide and lithium hydroxide. Preferably, the base is sodium hydroxide. The amount of base used will usually be 1.0-1.5 mol with respect to 1 mol of the nitrobenzofuran compound. The reaction temperature is comprised between 50 and 110° C. Preferably 75-100° C.

Surprisingly, the aforementioned reaction conditions (water and strong base) of the condensation step a) further allows the preparation of compound III in less than 10 hours, preferably in 5 hours or less. In addition, the reaction is environmentally friendly and industrially viable.

The mixture obtained upon completion of the condensation may be supplied directly to step b) although usually it can be supplied to step b) after post-treatment such as washing and extraction. Compound III may also be isolated by ordinary isolating treatment of the mixture or its treated product by concentration, crystallization or salt formation before being supplied to step b).

The second step (step b)) comprises the catalytic reduction of compound III in the presence of a catalyst in a solvent under hydrogen pressure of from 2 to 5 kg/cm$^2$, preferably 5 kg/cm$^2$, to yield compound 5-amino-3-[4-(3-di-n-butylamino-propoxy)benzoyl]-2-n-butylbenzofuran (I).

The catalyst used in this reduction is a metallic catalyst. Suitable metallic catalyst includes platinum- or palladium-based catalyst such as palladium on charcoal, palladium hydroxide, platinum on charcoal or platinum on alumina or platinum dioxide. More preferably, palladium on charcoal is used.

The solvent is selected from a range of aliphatic alcohols such as methanol, ethanol, isopropyl alcohol, butyl alcohol, etc. Methanol and ethanol are preferred.

Step b) does not necessarily require specific temperature conditions. Preferably, step b) is conducted at a temperature from 20 to 50° C.

The mixture obtained upon completion of the reduction contains compound I and it is preferably used in the next step of reaction after post-treatment such as washing and extraction.

However, it is desirable to isolate compound I with acceptable purity before being converted into dronedarone.

In an embodiment of the invention, compound I is purified via formation of acid addition salts. The acids used are selected from organic acids or inorganic acids. Examples of organic acids are benzenesulfonic acid, p-toluenesulfonic acid, oxalic acid, benzoic acid, maleic acid, fumaric acid, succinic acid, citric acid, tartaric acid, trifluoroacetic acid. Examples of inorganic acids are hydrochloric acid, hydrobromic acid, sulphuric acid and phosphoric acid. Preferred acid is oxalic acid. The treatment with acid may be carried out in the presence of a polar solvent. Examples of polar solvents include dimethylformamide (DMF), ethyl acetate, aliphatic ethers such as diethyl ether and tetrahydrofuran, aliphatic ketones such as acetone and methyl isobutyl ketone, alcohols such as methanol, ethanol and isopropanol and water. It is preferred to carry out the reaction in an alcohol, more preferably, methanol. A mixture of any of the above solvents may also be employed.

The preferred temperature at which the process is carried out depends on the solvent used. When methanol is used, the process is carried out at reflux temperature and the reaction is complete in 1 hour, approximately.

Once obtained the acid addition salt of compound I, a neutralization process follows. This neutralization step uses a base selected from sodium or potassium hydroxide, bicarbonate or carbonates, amines like ammonia, alkylamines, etc. The base may be added as a solution in water or as a solid. The solvents used in the neutralization are not particularly restricted. Examples of suitable solvents are aromatic hydrocarbon solvents such as toluene and xylene, and polar solvents like dimethylformamide (DMF), ethyl acetate, aliphatic ethers such as diethyl ether and tetrahydrofuran, aliphatic ketones such as acetone and methyl isobutyl ketone, alcohols such as methanol, ethanol and isopropanol and water. A mixture of any of the above solvents may be also used. Preferred solvents are a mixture of water with toluene.

The present invention is further illustrated by the following examples. They should in no case be interpreted as a limitation of the scope of the invention as defined in the claims.

EXAMPLES

Example 1

2-n-butyl-3-[4-(3-di-n-butylamino-propoxy)benzoyl]-5-nitrobenzofuran (III)

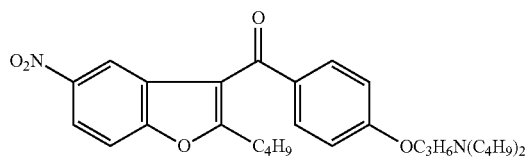

Example 1.1

In a 250 ml round bottom flask was charged 2-n-butyl-3-(4-hydroxybenzoyl)-5-nitrobenzofuran (10.0 g) (29.46 mmols), water (50.0 ml) and NaOH (1.18 g) (29.50 mmols) and stirred for 15 minutes. Heated the reaction mass to 80.0° C. and charged N,N-dibutyl-3-chloro-1-propanamine (9.09 g) (44.40 mmols) dropwise within 15 minutes. Reaction mass was maintained at 80.0° C. for 5 hours. At the end of this time the reaction mass was cooled at 30.0° C. and extracted in toluene (150.0 ml). The toluene layer was washed with 10.0% NaOH solution (50.0 ml×2) followed by water wash (50.0 ml×2). Finally the toluene layer was dried over sodium sulphate and concentrated to get reddish yellow oil (13.5 g).
Molar yield: 89.45%
HPLC purity: 93.22%

Example 1.2

In a 2.0 liter round bottom flask was charged 2-n-butyl 3-(4-hydroxy benzoyl) 5-nitrobenzofuran (200.0 g) (589.00 mmols), water (600.0 ml) and NaOH (35.39 g) (884.75 mmols) and stirred for 15 minutes. Heated the reaction mass to 90.0° C. and charged N,N-dibutyl-3-chloro-1-propanamine (120.45 g) (589.00 mmols) dropwise within 15 minutes. Reaction mass was maintained at 90.0° C. for 5 hours. At the end of this time the reaction mass was cooled at 30.0° C. and extracted in toluene (1500.0 ml). The toluene layer was washed with water (1000.0 ml×2). Finally the toluene layer was dried over sodium sulphate and concentrated to get reddish yellow oil (258.0 g).
Molar yield: 86.08%
HPLC purity: 97.92%

Example 2

5-amino 3-[4-(3-di-n-butylamino-propoxy)benzoyl]-2-n-butylbenzofuran (I)

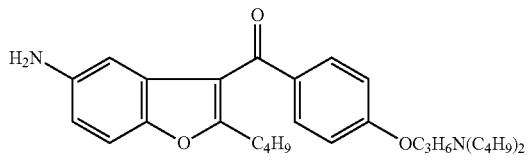

Example 2.1

Preparation of I (crude)

In 5.0 liter autoclave charged 2-n-butyl-3-[4-(3-di-n-butylamino-propoxy)benzoyl]-5-nitrobenzofuran (100.0 g) (196.85 mmols), ethanol (1000.0 ml) and 5% Pd/C (10.0 g) (50% moisture). Hydrogen pressure was applied up to 5.0 Kg/cm$^2$ at 30.0° C. and stirred the reaction mass for 6 hours. At the end of this time the reaction mass was filtered through hyflo bed. Filtrate was concentrated to give reddish yellow oil (91.0 g).
Molar yield: 96.80%
HPLC purity: 95.08%

Example 2.2

Preparation of I Dioxalate Salt

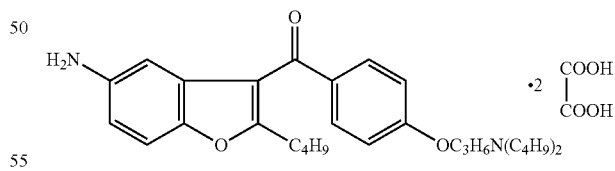

In a 250 ml round bottom flask was charged 5-amino-3-[4-(3-di-n-butylamino-propoxy)benzoyl]-2-n-butylbenzofuran (90.0 g) (177.16 mmols), methanol (450.0 ml) and stirred the solution for 10 minutes. To this reaction mass charged oxalic acid (37.28 g) (414.22 mmols) in one lot and heated the reaction mass to reflux for an hour. The reaction mass was cooled to 0° C. and stirred for an hour. The precipitated solid was filtered and dried at 50.0° C. under vacuum for 2 hours. (Dry weight: 104.0 g)
Molar yield: 84.00%
HPLC purity: 98.63%

Example 2.3

Preparation of I (Pure)

In a 50.00 ml round bottom flask was charged 5-amino-3-[4-(3-di-n-butylamino-propoxy)benzoyl]-2-n-butylbenzofuran dioxalate salt (80.0 g) (121.58 mmols), toluene (400.0 ml), water (400.0 ml) and stirred the reaction mass for 10 minutes. To this reaction mass was charged 10.0% (w/w) aqueous NaOH solution (95.0 ml) and stirred for 30 minutes. The pH of the reaction mass was maintained to ~10-12. At the end of this time, the toluene layer was separated and washed with water (400.0 ml×2). The toluene layer was separated, dried and concentrated to get yellow oil (53.0 g).
Molar yield: 91.20%
HPLC purity: 98.70%

Example 3

Preparation of I dioxalate salt

In 1.0 L autoclave charged 2-n-butyl 3-[4-(3-di-n-butylamino-propoxy)benzoyl]5-nitrobenzofuran (20.0 g) (39.37 mmols), methanol (140.0 ml) and 5% Pd/C (2.0 g) (50% moisture). Hydrogen pressure was applied up to 5.0 Kg/cm$^2$ at 30.0° C. and stirred the reaction mass for 6 hours. At the end of this time the reaction mass was filtered through hyflo bed. Filtrate was collected and transferred in 250.0 ml round bottom flask (Small sample was isolated and analyzed HPLC purity 92.36%). To this solution of 5-amino-3-[4-(3-di-n-butylamino-propoxy)benzoyl]-2-n-butylbenzofuran in methanol was added oxalic acid (7.78 g) (86.44 mmols) in one lot and heated the reaction mass to reflux for 1 hour. The reaction mass was cooled to 0° C. and stirred for 1 hour. The precipitated solid was filtered and dried at 50.0° C. under vacuum for 2 hours. (Dry weight: 18.0 g)
Molar yield: 69.49%
HPLC purity: 98.64%

Example 3.1

Preparation of I (Pure)

In a 50.00 ml round bottom flask was charged 5-amino-3-[4-(3-di-n-butylamino-propoxy)benzoyl]-2-n-butylbenzofuran dioxalate salt (17.0 g) (25.83 mmols), toluene (350.0 ml), water (100.0 ml) and stirred the reaction mass for 10 minutes. To this reaction mass was charged 10.0% (w/w) aqueous NaOH solution (20.0 ml) and stirred the reaction mass for 30 minutes. The pH of the reaction mass was maintained to ~10-12. At the end of this time the toluene layer was separated and washed with water (100.0 ml×2). The toluene layer was separated, dried and concentrated to get yellow oil (11.3 g).
Molar yield: 91.57%
HPLC purity: 98.61%

Example 4

Preparation of dronedarone base

Example 4.1

In a 250 ml round bottom flask was charged 5-amino-3-[4-(3-di-n-butylamino-propoxy)benzoyl]-2-n-butylbenzofuran (10.0 g) (20.92 mmols), toluene (100.0 ml) and heated to 110.0° C. Added dropwise the solution of methane sulfonyl chloride (2.10 ml in 10.0 ml of toluene) (27.01 mmols) and heated to reflux for 3 hours.

At the end of reaction, the reaction mass was cooled to 30.0° C. and charged saturated sodium bicarbonate solution (40.0 ml). The reaction mass was stirred for 10 minutes and toluene layer separated. Toluene layer was washed with water (50.0 ml×2) and dried over sodium sulphate (5.0 g).

Toluene layer was concentrated to get dronedarone base as thick oil (10.8 g).
Molar yield: 92.80%
HPLC purity: 96.69%

Example 4.2

In a 2.0 liter round bottom flask was charged 5-amino-3-[4-(3-di-n-butylamino-propoxy)benzoyl]-2-n-butylbenzofuran (100.0 g) (209.20 mmols), toluene (1000.0 ml) and heated at 110.0° C. Added dropwise the solution of methane sulfonylchloride (21.10 ml in 100.0 ml of toluene) (271.44 mmols) and heated to reflux for 3.0 hours.

At the end of reaction, the reaction mass was cooled to 30.0° C. and charged saturated sodium bicarbonate solution (500.0 ml). The reaction mass was stirred for 10 minutes and toluene layer separated. Toluene layer was washed with water (500.0 ml×2) and dried over sodium sulphate (50.0 g). Toluene layer was concentrated to get dronedarone base as thick oil (110.0 g).
Molar yield: 94.82%
HPLC purity: 97.30%

Example 5

Preparation of Dronedarone Hydrochloride

Example 5.1

Dronedarone Hydrochloride Crude (Using Ethereal HCl)

In a 2.0 L round bottom flask was charged 2-n-butyl-3-[4-(3-di-n-butyl amino propoxy)benzoyl]-5-methyl sulfonamido benzofuran (30.0 g) (53.95 mmols), ethyl acetate (1080.0 ml) and stirred at 30.0° C. for 10 minutes. To this solution the ethereal HCl was added till the pH of reaction mass becomes to 3-4. The reaction mass was stirred for 3 hours. The solid obtained was filtered and dried at 50.0° C. under vacuum for 2 hours (Dry weight: 28.0 g).
Molar yield: 87.50%
HPLC purity: 98.13%
DSC: 141.23° C.

Example 5.2

Dronedarone Hydrochloride Pure

In a 500.0 ml round bottom flask was charged dronedarone hydrochloride crude (25.0 g) (42.15 mmols) and acetone (375.0 ml) and heated the mixture to reflux for 1 hour. The reaction mass was allowed to cool at 30.0° C. and stirred for 2 hours. At the end of this time the solid falls out. The solid was filtered and dried at 50.0° C. under vacuum for 2 hours (Dry weight: 17.5 g).
Molar yield: 70.0%
HPLC purity: 99.53%
DSC: 143.90° C.

Example 5.3

Dronedarone Hydrochloride Crude (Using TMSCl/Water)

In a 250.0 ml round bottom flask was charged 2-n-butyl-3-[4-(3-di-n-butyl amino propoxy)benzoyl]-5-methyl sulfonamido benzofuran (5.0 g) (8.99 mmols), ethyl acetate (180.0 ml), Trimethyl silyl chloride (1.33 ml) (10.40 mmols) and stirred at 30.0° C. for 10 minutes. To this solution water (0.10 ml) (5.55 mmols) was added dropwise pH of the reaction mass was observed to be 2-3.

The reaction mass was stirred for 3 hours and the solid obtained was filtered and dried at 50.0° C. under vacuum for 2 hours (Dry weight: 5.2 g).
Molar yield: 97.56%
HPLC purity: 98.34%
DSC: 140.67° C.

Example 5.4

Dronedarone Hydrochloride Pure

In a 100.0 ml round bottom flask was charged dronedarone hydrochloride crude (4.0 g) (6.74 mmols) and acetone (60.0 ml) and heated the mixture to reflux for 1 hour. The reaction mass was allowed to cool at 30.0° C. and stirred for 2.0 hours. At the end of this time the solid falls out. The solid was filtered and dried at 50.0° C. under vacuum for 2 hours (Dry weight: 2.7 g).
Molar yield: 67.5%
HPLC purity: 99.43%
DSC: 143.20° C.

Example 5.5

Dronedarone Hydrochloride Crude (Using Dry HCl Gas)

In a 250.0 ml round bottom flask was charged 2-n-butyl-3-[4-(3-di-n-butyl amino propoxy)benzoyl]-5-methyl sulfonamido benzofuran (5.0 g) (8.99 mmols), ethyl acetate (180.0 ml), stirred at 30.0° C. for 10.0 minutes. To this solution dry HCl gas was passed till the pH of reaction mass becomes 2-4. The reaction mass was stirred for 3 hours. The solid was filtered and dried at 50.0° C. under vacuum for 2 hours (Dry weight: 5.0 g).
Molar yield: 93.80%
HPLC purity: 98.66%
DSC: 140.43° C.

Example 5.6

Dronedarone Hydrochloride Pure

In a 100.0 ml round bottom flask was charged dronedarone hydrochloride crude (4.0 g) (6.74 mmols) and acetone (60.0 ml) and heated the mixture to reflux for 1 hour. The reaction mass was allowed to cool at 30.0° C. the reaction mass was stirred for 2 hours. At the end of this time the solids falls out. The solid was filtered and dried at 50.0° C. under vacuum for 2 hours (Dry weight: 2.6 g).
Molar yield: 65.0%
HPLC purity: 99.36%
DSC: 143.57° C.

The invention claimed is:

1. A process for obtaining dronedarone or pharmaceutically acceptable salts thereof

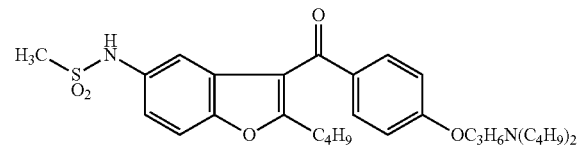

wherein, in an organic phase comprising one or more non-polar solvents selected from toluene, xylene, n-heptane, octane, isooctane, cyclohexane and 1,4-dioxane, 5-amino-3-[4-(3-di-n-butylamino-propoxy)benzoyl]-2-n-butylbenzofuran (I) is reacted with methane sulfonyl chloride, without the addition of a base, to give dronedarone, which optionally can be reacted with an organic or inorganic acid to form a pharmaceutically acceptable salt of dronedarone

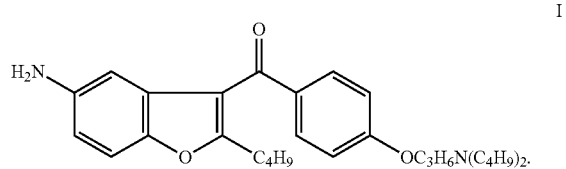

2. The process according to claim 1, wherein the non-polar solvent is toluene.

3. The process according to claim 1, wherein the acceptable salt of dronedarone is a hydrochloride salt.

4. The process according to claim 3, wherein dronedarone is reacted with trimethylsilyl chloride in the presence of water.

5. The process according to claim 1, wherein compound 5-amino-3-[4-(3-di-n-butylamino-propoxy)benzoyl]-2-n-butylbenzofuran (I) is prepared via:
   a) condensation of 2-n-butyl-3-(4-hydroxybenzoyl)-5-nitrobenzofuran (II)

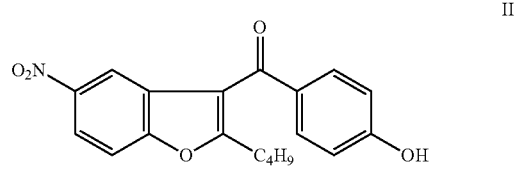

with N,N-butyl-3-chloro-1-propanamine in water and in the presence of a strong base to form 2-n-butyl-3-[4-(3-di-n-butylaminopropoxy)benzoyl]-5- nitrobenzofuran (III)

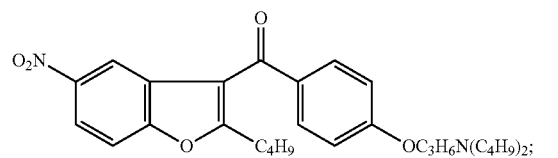

and b) catalytic reduction of compound III to obtain compound 5-amino-3-[4-(3-di-n-butylamino-propoxy)benzoyl]-2-n-butylbenzofuran (I)

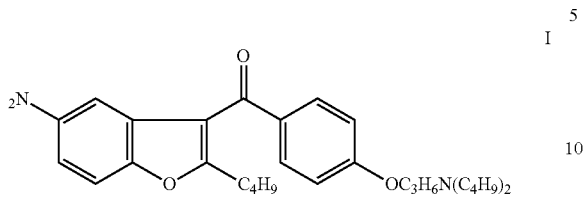

wherein the catalyst is a metallic catalyst selected from palladium on charcoal, palladium hydroxide, platinum on charcoal, platinum on alumina and platinum dioxide.

6. The process according to claim 5 wherein the strong base is selected from potassium hydroxide, barium hydroxide, cesium hydroxide, sodium hydroxide, strontium hydroxide, calcium hydroxide and lithium hydroxide.

7. The process according to claim 5 wherein the catalyst used in step b) is a metallic catalyst selected from platinum- or palladium-based catalyst.

8. The process according to claim 5 further comprising the step of formation of an acid addition salt of compound I.

9. The process according to claim 8 wherein the acid addition salt of compound I is formed with oxalic acid.

10. The process according to claim 8 further comprising a neutralization step with a base selected from sodium or potassium hydroxide, bicarbonate or carbonates, amines like ammonia and alkylamines.

\* \* \* \* \*